United States Patent [19]

Nyi et al.

[11] 4,140,724
[45] Feb. 20, 1979

[54] SELECTIVE PREPARATION OF POLYOL MONOETHERS OF DICYCLOPENTADIENE

[75] Inventors: Kayson Nyi, Sellersville; Alan W. Kohr, Schwenksville, both of Pa.

[73] Assignee: Rohm and Haas Company, Philadelphia, Pa.

[21] Appl. No.: 823,809

[22] Filed: Aug. 11, 1977

[51] Int. Cl.² .......................................... C07C 41/06
[52] U.S. Cl. .................................. 568/665; 568/633; 568/660
[58] Field of Search ............ 260/611 F, 614 A, 611 A, 260/613 D

[56] References Cited

U.S. PATENT DOCUMENTS

| | | | |
|---|---|---|---|
| 2,084,390 | 6/1937 | Dreyfus | 260/614 A |
| 2,162,913 | 6/1939 | Eversole et al. | 260/614 A X |
| 2,394,582 | 2/1946 | Bruson | 260/611 F |
| 2,480,940 | 9/1949 | Laum et al. | 260/614 A |
| 2,797,247 | 6/1957 | Keith | 260/614 A |
| 2,798,097 | 7/1957 | Hettinger et al. | 260/614 A |
| 3,345,419 | 10/1967 | Tinsley et al. | 260/611 F X |

*Primary Examiner*—Bernard Helfin
*Attorney, Agent, or Firm*—Lester E. Johnson

[57] ABSTRACT

Disclosed herein is an improved process for preparing an addition product of the reaction of a polyhydric compound and dicyclopentadiene, using a molar ratio of polyhydric compound to dicyclopentadiene of from about 1:4 to about 2:1, in the presence of an acid catalyst wherein the product comprises a hydroxyhydrocarbyl dihydrodicyclopentadiene represented by the formula

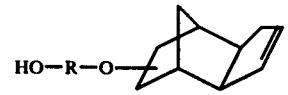

and wherein R is a divalent radical of 2 to 20 carbon atoms selected from the group consisting of saturated radicals, aromatic radicals and combinations thereof, the improvement comprising employing as the acid catalyst a crosslinked cation exchange resin having acid functionality.

19 Claims, No Drawings

SELECTIVE PREPARATION OF POLYOL MONOETHERS OF DICYCLOPENTADIENE

BACKGROUND OF THE INVENTION

Part A. Field of the Invention

This invention relates to the preparation of ethers by the reaction of polyhydric compounds with olefins in the presence of an acid catalyst. More particularly, it relates to the preparation of mono-ethers of polyhydric compounds by the addition reaction of polyhydric compounds with olefins in the presence of strong acid catalyst. More specifically, it relates to the selective preparation of mono-ethers of polyhydric compounds by reacting a poly-hydric compound with dicyclopentadiene in the presence of a crosslinked acid cation exchange resin.

Part B. Description of the Prior Art

The preparation of mono-ethers of polyhydric compounds by the addition reaction of a polyhydric compound and dicyclopentadiene in the presence of strong acid catalyst is known in the art. Bruson, U.S. Pat. No. 2,393,609 and Bruson and Riener, *J. Amer. Chem. Soc.*, 68, 8 (1946) disclose diol mono-ethers represented by the formula

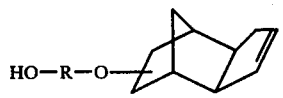

prepared by the addition reaction of a dihydric alcohol with dicyclopentadiene in the presence of a homogeneous strong acid catalyst such as a strong mineral acid catalyst or Lewis acid catalyst. Preparation of diol mono-ethers represented by formula I is problematic because of the lack of selectivity in the addition reaction between the starting diol and dicyclopentadiene. The product distribution, that is, unreacted diol, mono-ether and bis-ether, appears to be governed largely by statistics when the reaction is catalyzed with homogeneous strong acids such as sulfuric acid or boron trifluoride. Optimum yields of mono-ether, I, are obtained only when the addition reaction is carried out in the presence of a large excess, typically, greater than 100 mole percent excess, of diol. The use of excess diol reduces batch productivity and requires lengthened batch times in order to remove unused diol.

The substitution of acid functionalized cation exchange resins, particularly sulfonic acid functionalized resins, for strong mineral acid catalysts and Lewis acid catalysts in a variety of organic chemical reactions is known in the art. R. Kunin, "Ion Exchange Resins," 2d ed., John Wiley & Sons, Inc. New York, NY, 1958 pp. 255–259, discloses catalysis with cation exchange resin in a variety of applications. U.S. Pat. No. 3,037,052 to Bortnick discloses the use of an acid ion exchange resin in the place of conventional soluble strong acid as a catalyst in the esterification of a carboxylic acid with an olefin; the lactonization of a $\beta,\gamma$- or $\gamma,\delta$-unsaturated carboxylic acid; the alkylation of aromatic hydrocarbons and phenols; the condensation of ketones; the polymerization of olefins; and the acylation of olefins and aromatic compounds. Applications of ion exchange catalysis are also discussed in review articles by N. G. Polyanski in *Russian Chemical Reviews,* 31 (9), 496 (1962); 39 (3), 244 (1970). Further, the phenomenon referred to as "matrix enhancement", whereby the polymer matrix acts to increase the number of reactant/catalyst contacts over those obtained in homogeneous catalysis at equivalent reactant/catalyst concentrations, has been set forth in an industrial technical publication (A. R. Pitochelli, "Ion Exchange Catalysis and Matrix Effects," Fluid Process Chemicals, Rohm and Haas, 1975). However, the results from the substitution of ion exchange resin catalysts for conventional catalysts, and the achievement of any improvements thereby, are known in the art to be unpredictable.

It has been conceived and demonstrated herein that the problems of the prior art are overcome by this invention wherein the acid catalyst is provided as an acid functionality of a crosslinked cation exchange resin.

SUMMARY OF THE INVENTION

It is an object of this invention to provide an improved process for selectively preparing a mono-ether addition product of the reaction of a polyhydric compound and dicyclopentadiene in the presence of an acid catalyst.

This object, and others as will become apparent, is achieved by this invention which comprises, in an improved process for selectively preparing a mono-ether addition product, at the expense of bis-ether product, of the reaction of a polyhydric compound and dicyclopentadiene, using a molar ratio of polyhydric compound to dicyclopentadiene of from about 1:4 to about 2:1, in the presence of an acid catalyst, wherein the product comprises a hydroxyhydrocarbyl dihydrodicyclopentadiene represented by the formula

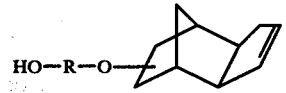

wherein R is a divalent radical of 2 to 20 carbon atoms selected from the group consisting of saturated radicals, aromatic radicals and combinations thereof, the improvement wherein the acid catalyst comprises a crosslinked cation exchange resin having acid functionality.

It has been discovered that a number of marked advantages are obtained by this invention wherein the addition reaction of a polyhydric compound and dicyclopentadiene makes use of an acid cation exchange resin as a catalyst rather than, solely, a conventional homogeneous strong acid catalyst such as a strong mineral acid, for example, sulfuric acid, or a Lewis acid, for example, boron trifluoride. In the process of this invention, the acid cation exchange resin may be used alone or in combination with homogeneous strong acids. The advantages over the prior art which are obtained by the process of this invention include increased selectivity of reaction in that higher yields of mono-ether may be obtained at the expense of bis-ether; reduction of the amount of excess polyhydric compound required for optimum yield to as low as 30 mole percent; convenient removal of catalyst from the reaction mixture; decreased corrosion of metallic apparatus used in the process of the invention; and recyclability of the catalyst. As an added advantage, when convenient, even an excess of dicyclopentadiene may be used in the process of the invention to obtain, selectively, the mono-ether product. In contrast, when an excess of dicyclopentadiene is used in the prior art using homogeneous acid catalyst, formation of bis-ether product is favored.

The polyhydric compound which may be used in this invention can be any member selected from the group consisting of dihydric and trihydric compounds wherein the hydroxy radicals of the polyhydric compound are bonded to a divalent radical of 2 to 20 carbon atoms selected from the group consisting of saturated radicals, aromatic radicals and combinations thereof. Suitable polyhydric compounds containing saturated radicals include straight-chain diols such as, for example, ethylene glycol, 1,3-propanediol, 1,6-hexanediol and triols such as, for example, glycerin; hexols derived from sugars such as, for example, mannitol; branched-chain diols such as, for example, 1,2-propylene glycol, 1,3-butylene glycol, neopentyl glycol, and 2-ethyl-1,3-hexanediol; alicyclic diols such as, for example, cyclohexane-1,6-diol; hetero-alicyclic diols such as, for example, 2,5-dimethylol-tetrahydrofuran; oligomers (i.e. polyols) of ethylene glycol, propylene glycol, and butylene glycol wherein the combined repeating units of the oxa-alkylene groups total up to about 20 atoms; and naturally occurring glycols. A suitable polyhydric compound containing an aromatic radical is, for example, 1,4-hydroquinone. Examples of polyhydric compounds comprising a mixture of saturated and aromatic radicals are 2-, 3-, and 4-hydroxybenzyl alcohols, 1,4-benzene dimethanol, and 1-phenyl-1,2-ethanediol.

Preferably, the polyhydric compound used in this invention is selected from the group consisting of dihydric compounds wherein the hydroxy radicals of the dihydric compound are bonded to a divalent radical of 2 to 8 carbon atoms selected from the group consisting of saturated radicals, aromatic radicals, and combinations thereof. More preferably, the polyhydric compound used in this invention is selected from the group consisting of 1,2- and 1,3-($C_2$–$C_8$) straight-chain and branched-chain dihydric saturated alcohols. Most preferably, the polyhydric compound used in this invention is selected from the group of $C_2$–$C_5$ dihydric compounds consisting of ethylene glycol, 1,2-propylene glycol, 1,3-propanediol, 1,3-butylene glycol and neopentyl glycol.

The acid functionality-containing crosslinked cation exchange resins which are used in this invention are known resins and are not claimed as new compositions of matter in themselves. Any of the known materials are suitable. The acid functionality of the resin may be a member selected from the group consisting of sulfonic, phosphonic, phosphinic, and carboxylic acid functional groups, which functionality imparts to the respective cation exchange resins a pka value of 6 or less (see Friedrich Helfferich, "Ion Exchange" McGraw-Hill, New York, NY, 1962, pp. 79–88). Generally, the resins which are useful in this invention may have either a gel or a macroreticular polymeric backbone which is functionalized with the acid functional groups set forth hereinabove. Suitable acid functionality-containing cation exchange resins within the scope of this invention are crosslinked macroreticular aromatic nuclear sulfonic, and carboxylic, acid resins such as, for example, those disclosed in U.S. Pat. No. 3,838,043; and macroreticular and gel phosphonic, and phosphinic, acid resins, the preparation of which is described in Friedrich Helfferich, "Ion Exchange," McGraw-Hill, New York, NY, 1962, pp. 32 and 38–39. As is known in the art, the acidity of the weakly acidic carboxylic acid resins may be increased by the presence of an electron-withdrawing group such as, for example, the cyano and trifluoromethyl groups, on the carbon atom in the $\alpha$-position with respect to the carboxylic acid group.

Preferably, the resins used in this invention are selected from the group of crosslinked strong acid cation exchange resins consisting of crosslinked macroreticular and gel aromatic nuclear sulfonic acid resin comprising a sulfonated polymer wherein the polymer is polymerized from a monomer mixture comprising from about 100% to about 1% by weight, based on total amount of monomer, of polyvinyl aromatic monomer, and wherein the resin is characterized as having an ion exchange capacity of from about 0.5 meq/g to about 5.0 meq/g. Suitable polyvinyl aromatic monomers include divinylbenzene, trivinylbenzene, divinyltoluene, divinylnaphthalene divinylpyridine, and diallylphthalate. The monomer mixture may further include up to about 99% by weight, based on total amount of monomer, of monovinyl aromatic monomer. Suitable monovinyl aromatic monomers include styrene and alkyl-substituted styrenes, halogen-substituted styrenes, vinylanisole, and vinylnaphthalene. While polyvinyl aromatic compounds are preferred as the crosslinking monomer used in the preparation of the preferred resin of this invention, other known polyunsaturated crosslinking monomers may optionally be used. Other suitable crosslinking monomers include, for example, ethylene glycol di(meth)acrylate and trimethylolpropane di(meth)acrylate and tri(meth)acrylate, allyl(meth)acrylate, diallyl maleate and the like.

More preferably, the resins used in this invention are selected from the group consisting of a macroreticular resin comprising a sulfonated macroreticular copolymer wherein the copolymer is polymerized from a monomer mixture comprising from about 85% to 10% by weight, based on total amount of monomer, of polyvinyl aromatic monomer and from about 15% to 90% by weight, based on total amount of monomer, of monovinyl aromatic monomer; and a gel resin comprising a sulfonated gel copolymer wherein the copolymer is polymerized from a monomer mixture comprising from about 20% to 1% by weight based on total amount of monomer of polyvinyl aromatic monomer and from about 80% to 99% by weight based on total amount of monomer of monovinyl aromatic monomer.

Most preferably, the resins used in this invention comprise a macroreticular resin comprising a sulfonated copolymer, wherein the copolymer is polymerized from a monomer mixture comprising from about 85% to 10% by weight of divinylbenzene and from about 15% to 90% by weight of styrene; and a gel resin comprising a sulfonated copolymer, wherein the copolymer is polymerized from a monomer mixture comprising from about 10% to 1% by weight of divinylbenzene and from about 90% to 99% by weight of styrene.

The ratio of amount of acid cation exchange resin (expressed as equivalents of acid functional group of the resin per mole of dicyclopentadiene or as "equivalent percent (%)" which is defined as the number of equivalents of acid functional group of the resin per mole of dicyclopentadiene multiplied by 100%) will vary widely depending on the nature of the acid cation exchange resin employed and on whether a batch, or a continuous, process is employed. In a batch process, the ratio of equivalents of resin per mole of dicyclopentadiene may vary from 0.001:1 to 0.5:1. A preferred ratio is from about 0.01:1 to 0.1:1.

The ratio of polyhydric compound to dicyclopentadiene can be varied over a wide range and still be within the scope of the invention. Since it is postulated that one hydroxy radical of the polyhydric compound reacts with one double bond of cicyclopentadiene, the ratios of these reactants may be expressed as molar ratios. Generally, a molar ratio of polyhydric compound to dicyclopentadiene of from about 1:4 to 2:1 may be used. When the polyhydric compound is the preferred dihydric compound, a preferred molar ratio of dihydric compound to dicyclopentadiene of from about 1.1:1 to about 2:1 may be employed. A molar ratio of dihydric compound to dicyclopentadiene of about 1.3:1 is most preferred.

Other reaction parameters such as time and temperature required will depend upon the specific polyhydric compound used in the addition reaction with dicyclopentadiene and upon whether a batch, or a continuous, process is employed.

Although the pressure employed is not critical, it is preferred to use a pressure at which the reactants will remain in a liquid condition. Atmospheric pressure is ordinarily satisfactory.

The scope of the resin-catalyzed polyhydric compound addition to dicyclopentadiene appears to be largely governed by the molecular size of the polyhydric compound, the pore size of the resin when the preferred macroreticular resins are employed, and the hydrophilicity of the polyhydric compound. The enhanced selectivity of the addition of dihydric compound with dicyclopentadiene observed with crosslinked macroreticular sulfonic acid cation exchange resins according to the invention probably results from the affinity of the resin for the dihydric compound. Within the resin interstices at the sites of catalytic activity, a large excess of dihydric compound exists. Therefore, dicyclopentadiene reacts in the presence of this large excess of dihydric compound which statistically favors mono-ether formation.

The process of this invention using a dihydric compound is described, generally, as follows:

A small excess (30 mole percent based on dicyclopentadiene) of dihydric compound is heated to 110° C. under nitrogen atmosphere in the presence of 3.5 equivalent percent crosslinked macroreticular sulfonic acid cation exchange catalyst. Dicyclopentadiene is then gradually added over 3 hours followed by a 3-hour hold, both at 110°–115° C. The resin is removed by filtration and is ready for recycling to the next batch without further treatment. The filtrate is then recharged to the reaction vessel and neutralized with 0.44 equivalent percent sodium hydroxide as a 50% aqueous solution to suppress "color throw" from the resin; excess dihydric compound is removed by distillation at reduced pressure; and the mono-ether product is isolated by distillation of the residue at reduced pressure.

The following examples are presented to illustrate but a few embodiments of the invention. All parts and percentages are by weight unless otherwise indicated. The data of record is not deemed to be limitative of the scope of the invention. Rather, it represents the current best mode available.

DESCRIPTION OF THE PREFERRED EMBODIMENTS

EXAMPLE 1

A reaction vessel equipped with a mechanical stirrer, a nitrogen inlet, an addition funnel, a condenser, a heating mantle, a thermometer, and an automatic temperature control device is charged with 80.6 g (1.3 mole) of anhydrous ethylene glycol and 7.6 g (0.035 equivalents, or 3.5 equivalent percent, of sulfonic acid) of a crosslinked, macroreticular sulfonic acid cation exchange resin having a styrene/divinyl benzene copolymeric matrix (such as, for example, Amberlyst ® 15, supplied by Rohm and Haas Company). The mixture is stirred and heated to about 110° C. under a nitrogen atmosphere 132 g (1 mole) of dicyclopentadiene is then gradually added over a period of 3 hours and then the mixture is held at 110°–115° C., for an additional 3-hour period. Analysis of the resulting crude product mixture by gas/liquid chromatography (glc) indicates the yield of mono-ether product to be about 89%.

The reaction mixture is then filtered to remove the resin catalyst, the filtered resin beads are washed with an additional portion of ethylene glycol, and the wash is combined with the filtrate. (In a large scale continuous process, the resin catalyst would be recycled to the succeeding batch). Sodium hydroxide (3.53 g of 50% aqueous solution, 0.0044 mole) is added to the filtrate prior to distillation of the filtrate in order to neutralize any free sulfonic acid which has been leached from the resin. If not neutralized, this free sulfonic acid will cause coloration ("color throw") of the mono-ether product during the distillation. ("Color throw", a phenomenon known in the art, is the diffusion of unattached or linear sulfonated polymer from the resin phase into the liquid phase during contact of the resin with a liquid).

Ethylene glycol is removed from the neutralized filtrate by distillation under reduced pressure of about 20 mm Hg. The mono-ether product is then distilled under reduced pressure to give, in several fractions, a combined yield of about 82% as a colorless liquid, b.p. 135°–145° C./6 mm Hg, the major fraction of distillate being collected at about 140° C./6 mm Hg.

EXAMPLES 2–8

Six additional hydroxyalkyl dicyclopentadiene mono-ethers are prepared by the procedure set forth in Example 1 by reacting six different diols with dicyclopentadiene in the presence of the crosslinked, macroreticular sulfonic acid cation exchange resin used in Example 1. The respective starting diols and the boiling points and pressures of the mono-ether products are set forth in TABLE I.

TABLE I

Hydroxyalkyl Mono-Ethers from Diols and Dicyclopentadiene

| Example No. | Starting Polyol[1] | Mono-ether Product Boiling Point/Pressure |
|---|---|---|
| 2 | 1,2-Propylene glycol | 94–102° C./0.05 mm Hg |
| 3 | 1,3-Propanediol | 134–135° C./1 mm Hg |
| 4 | 1,3-Butylene glycol | 100–103° C./0.05 mm Hg |
| 5 | Neopentyl glycol | 113–125° C./0.5 mm Hg |
| 6 | Dipropylene glycol | 125–135° C./0.1 mm Hg |
| 7 | 2-Ethyl-1,3-hexanediol | 150° C./0.6 mm Hg (slight-decomposition) |
| 8 | Glycerin | 167–170° C./0.5 mm Hg |

[1]The molar ratio of polyol:dicyclopentadiene is 1.3:1

EXAMPLES 9–13

The preparations of several typical hydroxyalkyl mono-ethers of dicyclopentadiene according to the invention are carried out using the sulfonic acid cation exchange resin catalyst employed in Example 1. For comparison, the same hydroxyalkyl mono-ether products are prepared using homogeneous 95% sulfuric acid as the catalyst.

TABLE II

Comparison of Sulfonic Cation Exchange Resin Catalysis and Homogeneous Sulfuric Acid Catalysis

| Example No. | Diol[4] | Catalyst (conc, equivalent %) | Yield of Mono-ether Determined by GLC Analysis |
|---|---|---|---|
| 9 | Ethylene glycol | resin catalyst[5] (3.5) | 90.8[2] |
|   |   | $H_2SO_4$ (2) | 51.0 |
| 10 | 1,2-Propylene glycol | resin catalyst[5] (3.5) | 68.9[3] |
|   |   | $H_2SO_4$ (2) | 58.3 |
| 11 | 1,3-Propanediol | resin catalyst[5] (3.5) | 70.1 |
|   |   | $H_2SO_4$ (2) | 53.1 |
| 12 | Neopentyl glycol | resin catalyst[5] (3.5) | 86.9 |
|   |   | $H_2SO_4$ (2) | 64.6 |
| 13 | 1,3-Butylene glycol | resin catalyst[5] (3.5) | 57.5 |
|   |   | $H_2SO_4$ (2) | 44.5 |

[1] Typically, isolated (distillation) yields are ca. 5% less than yields of mono-ether determined by GLC analysis. Methyl undec-10-enoate (b.p. 129–131° C./12 mm, purchased from City Chemical Corp.) was the internal standard. GLC analyses were performed on a 6' × 1", 5% OV-17 on Anachrom ABS column in a Varian Model 2700, dual column chromatograph equipped with flame ionization detectors.
[2] Bruson (U.S. 2,393,609) achieved isolated (distillation) yields of 51% (ethylene glycol:dicyclopentadiene ratio of 1:1) and 59% (ratio=1.5) using 17.6 mole % $BF_3$etherate catalyst and 19.4 mole % sulfuric acid catalyst, respectively.
[3] Bruson reported an isolated distillation yield of 59.1% using equimolar quantities of 1,2-propylene glycol and dicyclopentadiene.
[4] The molar ratio of diol:dicyclopentadiene is 1.3:1.
[5] The crosslinked, macroreticular sulfonic acid cation exchange resin used in Example 1 is employed as the acid catalyst.

The results presented in TABLE II for Examples 9–13 demonstrate that the process of this invention gives higher yields of the mono-ether product (at the expense of bis-ether product) than is obtained by the process of the prior art using homogeneous sulfuric acid catalyst.

Although the relationship is not understood, the molecular size of the diol appears to have an effect on the cation exchange resin catalyzed addition reaction with dicyclopentadiene. Among the smaller $C_2$–$C_5$ diols, the most pronounced selectivity obtained with the use of cation exchange resin catalysis according to the invention is observed in the addition reaction of ethylene glycol and neopentyl glycol with dicyclopentadiene which, when used in a molar ratio of 1.3:1, respectively, gives substantially higher yields than is obtained with the use of sulfuric acid. The cation exchange resin catalyzed addition reactions of 1,2-propylene glycol, 1,3-propanediol, and 1,3-butylene glycol with dicyclopentadiene also show improved selectivity over homogeneous acid catalyzed addition but to a lesser extent. 1,4-butanediol yields only tetrahydrofuran with either heterogeneous acid cation exchange resin, or homogeneous acid, catalyst.

EXAMPLES 14-(A-F)

The cation exchange resin catalyzed addition reaction of ethylene glycol with dicyclopentadiene, according to the invention, is carried out at varying molar ratios of the reactants in order to determine the effects of varying amounts of excess diol on the yield of mono-ether product. The results are presented in TABLE III.

TABLE III

Effect of Excess Diol on Product Distribution

| Example No. | Molar Ratio Ethylene Glycol:Dicyclopentadiene[1] | Yield of Mono-ether Determined by GLC Analysis |
|---|---|---|
| 14A | 1.1 | 77.3–78.9 |
| 14B | 1.2 | 79.7 |
| 14C | 1.3 | 88.5–90.8[2] |
| 14D | 1.5 | 87.9–89.3 |
| 14E | 1.7 | 87.3–88.2 |
| 14F | 2.0 | 89.5[3] |

[1] All of the reactions were catalyzed with 3.5 equivalent % of the crosslinked macroreticular sulfonic acid cation exchange resin used in Example 1 is employed as the acid catalyst.
[2] At this ratio, sulfuric acid catalysis affords 51% yield determined by GLC analysis.
[3] At this ratio, sulfuric acid catalysis affords 77% yield determined by GLC analysis.

The results shown in TABLE III indicate that 30 mole % excess diol is the minimal amount of excess at which optimal yields of mono-ether product is obtained in the acid cation exchange resin catalyzed addition reaction of ethylene glycol and dicyclopentadiene. Greater excesses of diol do not provide any improvement in yield of mono-ether product.

EXAMPLE 15

Samples of several different metals typically used in process kettle construction are exposed to an acid cation exchange resin catalyst which is within the scope of that used in the invention, and to a conventional homogeneous acid catalyst, 95% sulfuric acid. The results are presented in TABLE IV.

TABLE IV

Corrosive Effects of Catalysts on Metals

| Metal | Catalyst | Calculated Liquid Phase Corrosion Rate (mil/yr) |
|---|---|---|
| Monel | resin catalyst[1] | 11 |
| SS-304 |  | 1.6 |
| SS-304 | Sulfuric acid (95%) | 155 |
| SS-316 |  | 66 |
| Monel |  | 6.6 |

[1] The crosslinked, macroreticular sulfonic acid cation exchange resin used in Example 1 is employed as the acid catalyst.

The results shown in TABLE IV demonstrate that the sulfonic acid cation exchange resin catalyst is markedly less corrosive to SS-304 than is 95% sulfuric acid. The resin catalyst is slightly, although not significantly, more corrosive to Monel than is 95% sulfuric acid.

EXAMPLE 16

Example 1 is repeated except that 7.6 g (0.030 equivalents of sulfonic acid) of a crosslinked sulfonic acid cation exchange resin having a low-crosslinked styrene/divinyl benzene copolymeric matrix (such as, for example, Amberlite XE-200, H form, supplied by Rohm and Haas Company) is substituted for the macroreticular resin of Example 1. Analysis of the resulting crude product mixture by gas/liquid chromatography (GLC) indicates the yield of mono-ether product to be about 85% and the mono-ether product to be identical to that obtained in Example 1.

We claim:

1. In an improved process for selectively preparing a mono-ether addition product of the reaction of a anhydrous polyhydric compound having 2 to 20 carbon atoms and dicyclopentadiene, using a molar ratio of polyhydric compound to dicyclopentadiene of from about 1:4 to about 2:1 in the presence of an acid catalyst, wherein the product comprises a hydroxyhydrocarbyl dihydrodicyclopentadiene represented by the formula

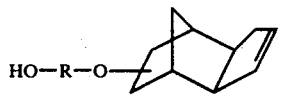

wherein R is a divalent radical of 2 to 20 carbon atoms selected from the group consisting of saturated radicals, unsaturated radicals, aromatic radicals and combinations thereof, the improvement wherein the acid catalyst comprises a crosslinked cation exchange resin having acid functionality.

2. The process of claim 1 wherein the resin is selected from the group consisting of sulfonic acid, phosphonic acid, phosphinic acid and carboxylic acid cation exchange resins having a pKa less than about 6.

3. The process of claim 2 wherein the resin is a sulfonic acid cation exchange resin having a pKa less than about 1.

4. The process of claim 3 wherein the resin comprises a sulfonated polymer wherein the polymer is polymerized from a monomer mixture comprising from about 100% to about 1% by weight, based on total amount of monomer, of polyvinyl aromatic monomer, and wherein the resin is characterized as having an ion exchange capacity of from about 0.5 meq/g to about 5.0 meq/g.

5. The process of claim 4 wherein the resin comprises a gel resin comprising a sulfonated gel polymer.

6. The process of claim 5 wherein the monomer mixture comprises from about 20% to 1% by weight, based on total amount of monomer, of polyvinyl aromatic monomer and from about 80% to about 99% by weight, based on total amount of monomer, of monovinyl aromatic monomer.

7. The process of claim 6 wherein the monomer mixture comprises from about 10% to 1% by weight of divinyl benzene and from about 90% to 99% by weight of styrene.

8. The process of claim 4 wherein the resin comprises a macroreticular resin comprising a sulfonated macroreticular polymer.

9. The process of claim 8 wherein the monomer mixture comprises from about 85% to 10% by weight, based on total amount of monomer, of polyvinyl aromatic monomer and from about 15% to 90% by weight, based on total amount of monomer, of monovinyl aromatic monomer.

10. The process of claim 9 wherein the polyvinyl aromatic monomer is divinylbenzene and the monovinyl monomer is styrene.

11. The process of claim 1 wherein the polyhydric compound is selected from the group consisting of dihydric and trihydric compounds wherein the hydroxy radicals of the polyhydric compound are bonded to a divalent radical of 2 to 20 carbon atoms selected from the group consisting of saturated radicals, unsaturated radicals, aromatic radicals and combinations thereof.

12. The process of claim 3 wherein the polyhydric compound is selected from the group consisting of dihydric compounds wherein the hydroxy radicals of the dihydric compound are bonded to a divalent radical of 2 to 8 carbon atoms selected from the group consisting of saturated radicals, aromatic radicals and combinations thereof.

13. The process of claim 4 wherein the polyhydric compound is selected from the group consisting of dihydric compounds wherein the hydroxy radicals of the dihydric compound are bonded to a divalent radical of 2 to 8 carbon atoms selected from the group consisting of saturated radicals, aromatic radicals and combinations thereof.

14. The process of claim 5 wherein the polyhydric compound is selected from the group consisting of 1,2- and 1,3-($C_2$-$C_8$) straight-chain and branched-chain saturated dihydric alcohols.

15. The process of claim 6 wherein the polyhydric compound is selected from the group consisting of 1,2- and 1,3-($C_2$-$C_8$) straight-chain and branched-chain dihydric saturated radicals.

16. The process of claim 7 wherein the polyhydric compound is selected from the group of ($C_2$-$C_5$) dihydric alcohols consisting of ethylene glycol, 1,2-propylene glycol, 1,3-propanediol, 1,3-butylene glycol, and neopentyl glycol.

17. The process of claim 8 wherein the polyhydric compound is selected from the group consisting of 1,2- and 1,3-($C_2$-$C_8$) straight-chain and branched-chain saturated dihydric alcohols.

18. The process of claim 9 wherein the polyhydric compound is selected from the group consisting of 1,2- and 1,3-($C_2$-$C_8$) straight-chain and branched-chain dihydric saturated radicals.

19. The process of claim 10 wherein the polyhydric compound is selected from the group of ($C_2$-$C_5$)dihydric alcohols consisting of ethylene glycol, 1,2-propylene glycol, 1,3-propane diol, 1,3-butylene glycol, and neopentyl glycol.

* * * * *

Dedication 4,140,724.—*Kayson Nyi*, Sellersville and *Alan W. Kohr*, Schwenksville, Pa. SELECTIVE PREPARATION OF POLYOL MONOETHERS OF DICYCLOPENTADIENE. Patent dated Feb. 20, 1979. Dedication filed Mar. 7, 1980, by the assignee, *Rohm and Haas Company*. Hereby dedicates to the Public the entire term of said patent.
[*Official Gazette, May 20, 1980.*]